(12) United States Patent
Gupta et al.

(10) Patent No.: US 9,029,129 B2
(45) Date of Patent: May 12, 2015

(54) STREAKING APPLICATOR CARTRIDGE AND A SYSTEM FOR CONNECTING SAME TO A STREAKING APPARATUS

(75) Inventors: Rajiv Gupta, Cupertino, CA (US); Stephen Lewis Leckenby, Victoria (CA); Phillip James Duncan, Mount Waverly (AU); Ryan Andrew Annear, South Carlton (AU); Colin William Potter, Nunawading (AU)

(73) Assignee: LBT Innovations Limited, Adelaide SA (AU)

( * ) Notice: Subject to any disclaimer, the term of this patent is extended or adjusted under 35 U.S.C. 154(b) by 1333 days.

(21) Appl. No.: 12/520,974

(22) PCT Filed: Jan. 11, 2008

(86) PCT No.: PCT/AU2008/000015
§ 371 (c)(1),
(2), (4) Date: Dec. 14, 2009

(87) PCT Pub. No.: WO2008/083438
PCT Pub. Date: Jul. 17, 2008

(65) Prior Publication Data
US 2010/0099181 A1    Apr. 22, 2010

(30) Foreign Application Priority Data

Jan. 12, 2007  (AU) ................................ 2007900144

(51) Int. Cl.
*C12M 1/26*    (2006.01)
*C12M 3/00*    (2006.01)
(Continued)

(52) U.S. Cl.
CPC ............... *C12M 99/00* (2013.01); *C12M 33/04* (2013.01); *A61B 10/0096* (2013.01)

(58) Field of Classification Search
CPC ........ C12M 99/00; C12M 1/26; C12M 1/261; C12M 1/30; C12M 33/04; A61B 10/0096; B01L 2300/0838
USPC ....................................................... 435/309.1
See application file for complete search history.

(56) References Cited

U.S. PATENT DOCUMENTS

| | | |
|---|---|---|
| 3,455,788 A | 7/1969 | Curry et al. |
| 3,623,958 A | 11/1971 | Fitzgerald et al. |
| 3,632,478 A | 1/1972 | Fink |

(Continued)

FOREIGN PATENT DOCUMENTS

| | | |
|---|---|---|
| CA | 1286621 C | 7/1991 |
| DE | 19520420 C2 | 12/1996 |

(Continued)

*Primary Examiner* — Michael Hobbs
(74) *Attorney, Agent, or Firm* — Seager, Tufte & Wickhem LLC (57) ABSTRACT

A cartridge for holding and dispensing streaking applicators for an automated streaking apparatus having a cartridge holder, the cartridge including: a case with a dispensing end, a longitudinal axis and an elongate slot generally parallel to the longitudinal axis, the dispensing end including an applicator dispensing position where one applicator can be at least partially accessible from outside the case; and an applicator support member constrained within the case for longitudinal movement therein and being able to carry a stack of applicators; the elongate slot being capable of operatively receiving a biasing member when the cartridge is in the cartridge holder to urge the support member towards the dispensing end and an applicator into the dispensing position.

6 Claims, 6 Drawing Sheets

(51) Int. Cl.
*C12M 1/00* (2006.01)
*A61B 10/00* (2006.01)

(56) References Cited

U.S. PATENT DOCUMENTS

| | | | |
|---|---|---|---|
| 3,660,243 A | 5/1972 | Young | |
| 3,778,351 A | 12/1973 | Rosov | |
| 3,788,951 A | 1/1974 | von der Pfordten | |
| 3,799,844 A | 3/1974 | Campbell et al. | |
| 3,830,701 A | 8/1974 | Stussman et al. | |
| 3,850,754 A | 11/1974 | Wilkins et al. | |
| 3,935,075 A | 1/1976 | Perry et al. | |
| 3,962,040 A | 6/1976 | Campbell et al. | |
| 4,010,077 A | 3/1977 | Pardos | |
| 4,102,748 A | 7/1978 | Vacanti | |
| 4,144,135 A | 3/1979 | Sequeira | |
| 4,170,861 A | 10/1979 | Snyder et al. | |
| 4,279,861 A * | 7/1981 | Jessop | 422/67 |
| 4,287,301 A | 9/1981 | Astle | |
| 4,613,573 A | 9/1986 | Shibayama et al. | |
| 4,687,746 A | 8/1987 | Rosenberg et al. | |
| 4,892,831 A | 1/1990 | Wong | |
| 4,981,802 A | 1/1991 | Wylie et al. | |
| 5,106,584 A | 4/1992 | Funakubo et al. | |
| 5,206,171 A | 4/1993 | Dillon et al. | |
| 5,447,690 A * | 9/1995 | Sugaya | 422/64 |
| 5,629,201 A | 5/1997 | Nugteren et al. | |
| 5,691,195 A | 11/1997 | Doleans et al. | |
| 5,695,988 A | 12/1997 | Chong | |
| 5,756,304 A | 5/1998 | Jovanovich | |
| 6,291,234 B1 | 9/2001 | Raz et al. | |
| 6,521,190 B1 | 2/2003 | Edens et al. | |
| 6,617,146 B1 | 9/2003 | Naccarato et al. | |
| 6,843,962 B2 | 1/2005 | Haslam et al. | |
| 6,932,527 B2 | 8/2005 | Pribula et al. | |
| 7,709,268 B1 | 5/2010 | Edwards et al. | |
| 2001/0024832 A1 * | 9/2001 | Seto et al. | 436/46 |
| 2002/0064867 A1 | 5/2002 | Clark et al. | |
| 2002/0120214 A1 | 8/2002 | Cole | |
| 2004/0191121 A1 * | 9/2004 | Tomasso et al. | 422/65 |
| 2007/0202564 A1 | 8/2007 | Glasson et al. | |
| 2008/0318310 A1 | 12/2008 | Dufresne et al. | |

FOREIGN PATENT DOCUMENTS

| | | |
|---|---|---|
| FR | 2668495 A1 | 4/1992 |
| GB | 2025457 A | 1/1980 |
| GB | 2247076 A | 2/1992 |
| GB | 2255407 A | 11/1992 |
| GB | 2 411 894 A | 9/2005 |
| JP | 01191678 B | 8/1989 |
| JP | 02072898 A | 3/1990 |
| JP | 03049676 A | 3/1991 |
| JP | 03061476 A | 3/1991 |
| JP | 03133375 A | 6/1991 |
| JP | 03175996 A | 7/1991 |
| JP | 04234973 A | 8/1992 |
| JP | 04248980 A | 9/1992 |
| JP | 05225995 A | 9/1993 |
| JP | 05344535 A | 12/1993 |
| JP | 06225753 A | 8/1994 |
| JP | 06296481 A | 10/1994 |
| JP | 07067695 A | 3/1995 |
| JP | 07170970 A | 7/1995 |
| JP | 10004952 A | 1/1998 |
| JP | 10309199 A | 11/1998 |
| JP | 11346796 A | 12/1999 |
| JP | 2001149062 A | 6/2001 |
| JP | 2001149063 A | 6/2001 |
| JP | 2001153761 A | 6/2001 |
| JP | 2002098704 A | 4/2002 |
| JP | 3414431 B2 | 6/2003 |
| JP | 2005052069 A | 3/2005 |
| JP | 2008166201 A | 7/2008 |
| WO | 8808024 A1 | 10/1988 |
| WO | 0166686 A1 | 9/2001 |
| WO | 2004022245 A1 | 3/2004 |
| WO | 2005/071055 A1 | 8/2005 |

* cited by examiner

Figure 6

STREAKING APPLICATOR CARTRIDGE AND A SYSTEM FOR CONNECTING SAME TO A STREAKING APPARATUS

This international patent application claims priority from Australian provisional patent application 2007900144 filed on 12 Jan. 2007 and PCT/AU 2008/000015 filed on Jan. 11, 2008, the contents of which are to be taken as incorporated herein by this reference.

FIELD OF THE INVENTION

The present invention relates generally to apparatus involved in the inoculation of solid growth culture media with a microbiological sample, and the subsequent streaking of the inoculum to produce isolated bacterial colonies, principally for diagnostic purposes in a laboratory, such as for medical diagnostic purposes. The present invention specifically relates to cartridges used for the transportation and storage of streaking applicators, and for the subsequent dispensing of the streaking applicators to an automated streaking apparatus, together with a system for the connection of those cartridges to such an automated streaking apparatus.

BACKGROUND OF THE INVENTION

The isolation of individual colonies of micro-organisms (and in particular bacteria) is an important procedure in many microbiological laboratories. Traditionally, this isolation of bacteria has been performed manually by skilled laboratory technicians who first dispense a microbiological sample onto the surface of a solid growth culture medium, such as agar in a Petri dish (which will hereafter simply be referred to as a "medium" in an "agar plate" or simply in a "plate"), followed by the use of a hand-tool to spread the sample across the surface of the medium (called "streaking").

The hand-tool typically includes a terminal loop to make multiple streaks of increasing dilution of the inoculum across the medium. The streaks of increasing dilution tend to provide, generally towards the tail of the streaks, a number of single cells that allow for the growth of isolated microbiological colonies after incubation. These isolated colonies may then be analysed for colony morphology, and may undergo staining and other procedures which are necessary for determining, for example, the genus, the species and the strain of the previously unidentified organism.

Such inoculation and streaking is highly repetitious and in many pathology diagnostic microbiology laboratories is usually conducted in very high volumes, such as in volumes as high as 1,000 to 15,000 plates per day. It is tedious and laborious work that therefore is prone to error and inaccuracies. It is quite obviously work that would lend itself to either partial or full automation.

The literature is replete with suggestions for how best to automate these laboratory functions, yet very few of these suggestions have ever actually found success in a commercial laboratory environment. It therefore appears that the successful enablement of suitable laboratory apparatus has to date, for most, proved elusive.

Three recent suggestions for the automation of these laboratory functions can be found in the following documents; U.S. Pat. No. 4,981,802 (C. Wylie et al) titled "Method and Apparatus for Streaking a Culture Medium", U.S. Pat. No. 6,617,146 (F. Naccarato et al) titled "Method and Apparatus for Automatically Inoculating Culture Media With Bacterial Specimens From Specimen Containers", and international patent publication WO2005/071055 (Medvet Science Pty Ltd) titled "Microbial Streaking Device" (licensed to the present applicant).

The Wylie and Naccarato patents describe automated and semi-automated apparatus that utilize re-usable streaking tools similar to the hand streaking tools mentioned above. However, the Medvet Science publication describes the use of a new form of streaking tool, being a streaking applicator that includes a line of spaced apart contact surfaces (for contact with the surface of solid growth media), the contact surfaces being resiliently flexibly supported by a common support member. This streaking applicator is intended to be a single use applicator, and thus be disposable. It has been found to permit greater spread of a larger volume of the inoculum across the surface of the medium with a single streaking pass, as well as larger areas of more gradually increasing dilution of the sample, and has proven to more readily permit automation of the streaking process.

It is an aim of the present invention to provide a cartridge that is able to be used for the transportation and storage of such streaking applicators, and for the subsequent dispensing of the streaking applicators to an automated streaking apparatus, together with a system for the connection of those cartridges to such an automated streaking apparatus.

Before turning to a summary of the present invention, it must be appreciated that the above description of the prior art has been provided merely as background to explain the context of the invention. It is not to be taken as an admission that any of the material referred to was published or known, or was a part of the common general knowledge in Australia or elsewhere.

It is also useful to provide an explanation of some of the terms that will be used to define the spatial relationship of the cartridge and connection system. In this respect, spatial references throughout this specification will generally be based upon a plate ultimately being inoculated and streaked in an upright orientation in an automated streaking apparatus, with the surface of the medium in the plate being generally flat and horizontal. With this environment as the basis, the cartridge and some parts thereof may then be defined with reference to the "horizontal", allowing further references to "upper" or "upwardly" and "lower" or "downwardly", and also to the "vertical". In this respect, the traditional geometric spatial reference to x, y and z dimensions, and then to the x direction (or axis), the y direction (or axis) and the z direction (or axis), may also be adopted, with the x and y directions lying generally horizontally and the z direction lying generally vertically.

Finally, some aspects of the present invention that may ultimately be claimed in isolation (and not in an in-use environment), may nonetheless be difficult to describe and understand in isolation. Thus, some of the following description does describe the invention and its embodiments in such an in-use environment (for example, with a streaking applicator in place within a cartridge, or a cartridge in place within an automated streaking apparatus). Of course, it must be appreciated that the use of such description, and the use of the abovementioned spatial relationships, to define the present invention, is not to be seen as a limitation and certainly is not to be seen as a limitation only to the in-use environment, unless this has been clearly stated to be the intention.

SUMMARY OF THE INVENTION

The present invention provides a cartridge for holding and dispensing streaking applicators for an automated streaking apparatus having a cartridge holder, the cartridge including:

a case with a dispensing end, a longitudinal axis and an elongate slot generally parallel to the longitudinal axis, the dispensing end including an applicator dispensing position where one applicator can be at least partially accessible from outside the case; and an applicator support member constrained within the case for longitudinal movement therein and being able to carry a stack of applicators;

the elongate slot being capable of operatively receiving a biasing member when the cartridge is in the cartridge holder to urge the support member towards the dispensing end and an applicator into the dispensing position.

The present invention also provides a loaded cartridge for holding and dispensing streaking applicators for an automated streaking apparatus having a cartridge holder, the loaded cartridge including:

a case with a dispensing end, a longitudinal axis and an elongate slot generally parallel to the elongate slot, the dispensing end including an applicator dispensing position where one applicator is at least partially accessible from outside the case; and an applicator support member carrying a stack of applicators, the support member being constrained within the case for longitudinal movement therein;

the elongate slot being capable of operatively receiving a biasing member when the cartridge is in the cartridge holder to urge the support member towards the dispensing end and an applicator into the dispensing position.

The present invention also provides a system for the connection of a loaded cartridge to a cartridge holder of an automated streaking apparatus, the cartridge being for the holding and dispensing of streaking applicators, the system including:

a cartridge holder having a biasing member; and a loaded cartridge having a case with a dispensing end, a longitudinal axis and an elongate slot generally parallel to the elongate slot, the dispensing end including an applicator dispensing position where one applicator is at least partially accessible from outside the case, the cartridge also including an applicator support member carrying a stack of applicators, the support member being constrained within the case for longitudinal movement therein;

the elongate slot being capable of operatively receiving the biasing member when the cartridge is in the cartridge holder to urge the support member towards the dispensing end and an applicator into the dispensing position.

As evident from the above, the cartridge of the present invention is suitable for use with a cartridge holder of an automated streaking apparatus, and the primary functions of the cartridge are the holding and dispensing of streaking applicators for use with that apparatus. The automated streaking apparatus is ideally of the type generally described in the present applicant's international patent application filed on 11 Jan. 2008 titled "Method and Apparatus for Inoculating and Streaking a Medium in a Plate", claiming priority from Australian provisional patent application 2007900146, the full content of which is hereby incorporated by reference. For present purposes, that streaking apparatus generally includes:

(a) a plate supply capable of storing raw plates in an inverted orientation;

(b) a plate transfer feed mechanism capable of obtaining an inverted raw plate from the plate supply, removing the lid from the raw plate, and transferring the orientated and de-lidded raw plate to a plate work position in an inoculating and streaking station;

(c) an inoculating device capable of dispensing inoculum on the surface of the medium in the positioned plate;

(d) a streaking device capable of obtaining a streaking applicator from a streaking applicator supply and then moving the streaking applicator such that its line of spaced apart contact surfaces contacts the surface of the medium in the positioned plate, prior to rotation of the positioned plate for streaking;

(e) a plate store capable of storing processed plates in an inverted orientation; and (f) a plate transfer store mechanism capable of retrieving a processed plate from the plate work position, re-orientating and re-lidding the processed plate, and transferring the processed plate to the plate store.

In one form of the present invention (although not the only form thereof), the cartridge is intended to be suitable for use as the streaking applicator supply for the above described automated streaking apparatus.

Furthermore, the streaking applicators described as being suitable for use with the above described automated streaking apparatus, namely the streaking applicators generally described in the abovementioned international patent publication WO2005/071055 (Medvet Science Pty Ltd) titled "Microbial Streaking Device" (licensed to the present applicant), the full content of which is also herein incorporated by reference, are envisaged to be the principal type of streaking applicator (although not the only type of streaking applicator) that the cartridge of the present invention is preferably configured to receive, hold and dispense. In this respect, these streaking applicators can be said to have a generally flat rectangular form, albeit with two major inclined portions that together form a very shallow inverted v-shaped body. An upper portion of the body provides a mounting portion and a lower portion of the body provides the line of spaced apart contact surfaces and a resilient and flexible support member.

Before turning to a general description of the various preferred elements of the cartridge itself, it is useful to generally describe the preferred form of cartridge holder that forms a part of the streaking apparatus and that thus forms a part of the inventive system for the connection of a loaded cartridge to a cartridge holder of an automated streaking apparatus. In this respect, the streaking apparatus may include multiple cartridge holders in order to be able to hold multiple cartridges and thus store, ready for dispensing, a very large number of streaking applicators, in a manner such that the streaking device mentioned above is able to selectively access any one of the cartridges to obtain a streaking applicator.

Preferably, each cartridge holder includes a housing configured and sized so as to receive a cartridge within its interior, ideally to slidably receive the cartridge in a close fit therein. The housing preferably includes either therewithin or as a part thereof, the biasing member mentioned above that operatively interacts with the elongate slot of the casing and the applicator support member. The housing also preferably includes a cartridge lock that releasably engages with the cartridge when in the cartridge holder to secure the cartridge in place. With regard to the reference to "operative" interaction, it will be appreciated that the use of this word merely indicates that interaction by an element with another element is to be such that either or both elements (as required) are then able to perform their required functions. The same applies for a reference to the terms "operatively receiving" or "operatively accessing" or the like.

The housing is preferably configured and oriented such that, when the cartridge is received therein, the applicator dispensing position of the cartridge can be operatively accessed by the streaking device of the streaking apparatus. In this respect, the housing need not be a fully enclosed housing, in that it includes complete side walls or the like. Indeed, in one form, it is envisaged that the housing will be generally provided by a suitable upright frame made up of four corner posts defining therewithin the cartridge receiving interior.

Turning now to a general description of the cartridge of the present invention, as mentioned above the cartridge includes a case with a dispensing end, a longitudinal axis and an elongate slot generally parallel to the elongate slot, the dispensing end of the case including the applicator dispensing position where one applicator (and preferably at least the mounting portion of one applicator) is operatively accessible from outside the case. The cartridge also includes the applicator support member that is constrained within the case for longitudinal movement therein and is able to carry a stack of applicators. Then, the elongate slot is capable of operatively receiving the biasing member of the cartridge holder when the cartridge is in the cartridge holder to urge the support member towards the dispensing end and an applicator into the dispensing position.

The case is preferably generally cylindrical with a rectangular cross-section, thereby having four side walls, a bottom wall (in the preferred form, being that wall at the end of the case opposite to the dispensing end), and a top wall (in this form, being the wall at the dispensing end). This preferred orientation illustrates that the cartridge is ideally elongate and is used in a generally upright orientation. Preferably the top wall only partially covers the dispensing end, there being at least one opening in the top wall to provide the streaking device with gripping access to an applicator in the applicator dispensing position, and at least one other opening through which the applicator may pass to be removed from the cartridge by the streaking device.

In this form, the top wall thus includes an upper applicator-gripping opening and a side applicator-dispensing opening, the gripping opening being sized to reveal the mounting portion of an applicator in the dispensing position, and the dispensing opening being sized to permit that applicator to be slid sideways from the stack of applicators from under the top wall out of the cartridge. Preferably the top wall is configured to conform to the shape of an applicator such that the uppermost applicator in the stack (being the applicator in the dispensing position) neatly abuts against the underside of the top wall due to the urging of the biasing member mentioned above, in which position the mounting portion of that applicator is accessible through the gripping opening and the applicator itself is removable via the dispensing opening.

Thus, the applicator support member that is constrained within the case for longitudinal movement therein is also preferably rectangular in cross-section and is sized for sliding movement within the case. In this form, the support member preferably includes ratchet-type resiliently biased engaging members on two of the opposed sides thereof, capable of engaging with a series of corresponding abutments along opposed interior surfaces of two of the side walls of the case, in a manner that only permits one way movement of the support member (in response to the urging towards the dispensing end by the biasing member of the cartridge holder) towards the dispensing end of the case.

In relation to this urging of the support member towards the dispensing end by the biasing member, the biasing member is preferably a biased abutment configured at least partially within the housing of the cartridge holder, the abutment being sized and located so as to fit within, and be received by, the elongate slot of the cartridge. In a preferred form, the biasing is provided by a spring, such as by a torsion spring.

The elongate slot is preferably arranged longitudinally along one of the side walls of the case, extending into the bottom wall of the case to allow inserting access of the abutment into the slot from below when the cartridge is slid into the housing.

Thus, when a loaded cartridge, loaded with a stack of applicators supported within the case upon the support member, is slid into the housing, the abutment enters the slot and engages with the underside of the support member. The biasing of the abutment is then such as to continuously urge the support member towards the dispensing end of the case so that the uppermost applicator in the stack is always urged into, and held in, the dispensing position.

Indeed, it will thus be apparent that the removal (or dispensing) of this uppermost applicator (in the manner described above) will then result in the next applicator (now being the uppermost applicator) in the stack again being urged by the biasing member into the dispensing position. This can then continue until the last applicator in the stack is dispensed and the cartridge is empty.

Upon emptying of the cartridge, it may be removed from the automated streaking apparatus and either disposed of for replacement by a new cartridge, returned to a supplier for re-charging, or re-filled by the user with a new stack of applicators. With this in mind, the case of the cartridge may be formed such that one of the four walls is detachably removable to provide easy access to the interior thereof such that the cartridge can be re-loaded. In this form, the removable wall would preferably be the side wall opposite the elongate slot.

BRIEF DESCRIPTION OF THE DRAWINGS

Having briefly described the general concepts involved with the present invention, a preferred embodiment will now be described that is in accordance with the present invention. However, it is to be understood that the following description is not to limit the generality of the above description.

In the drawings.

DESCRIPTION OF A PREFERRED EMBODIMENT

Figure 1:
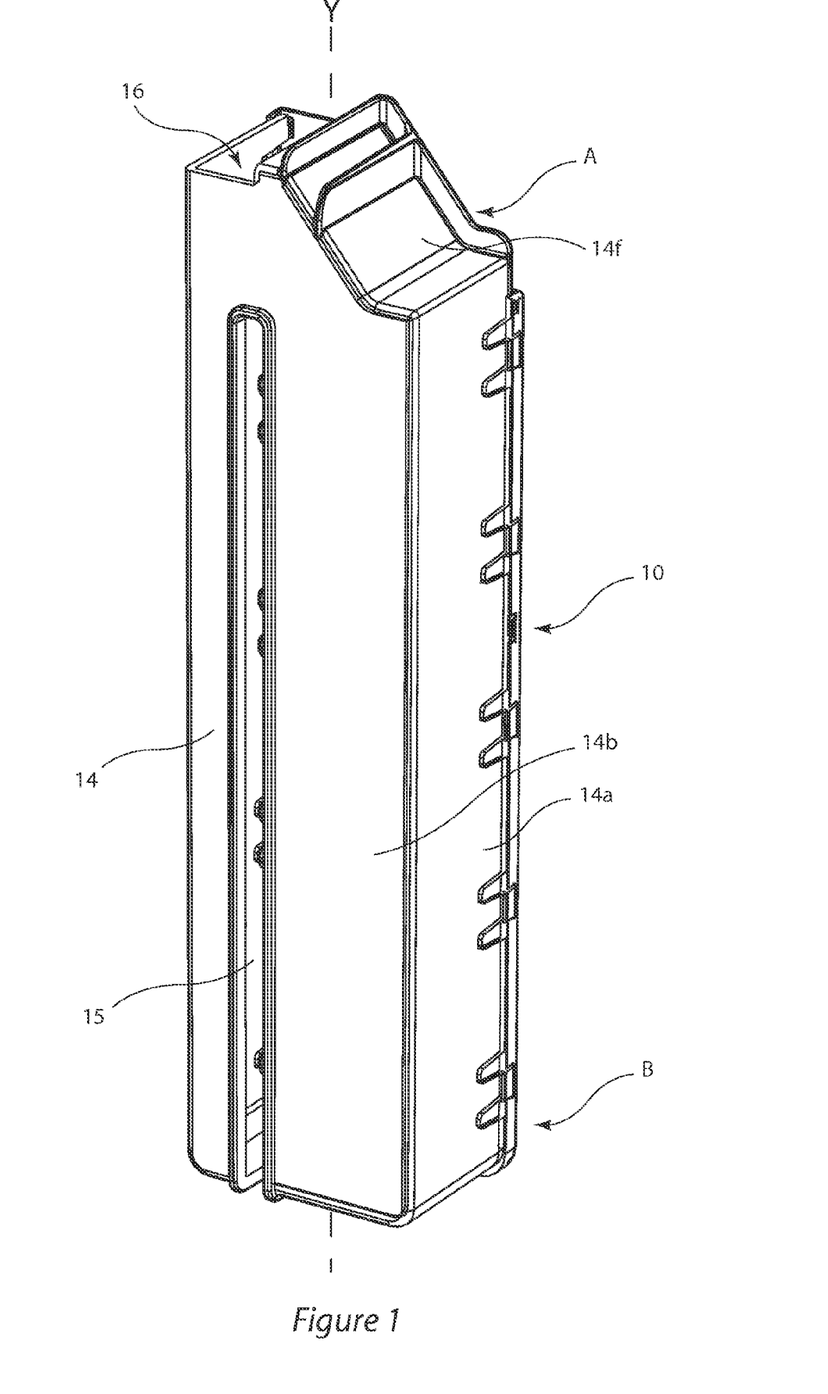
FIG. 1 is a perspective view from one side and from above of a cartridge in accordance with a preferred embodiment of the present invention.
Figure 2A:
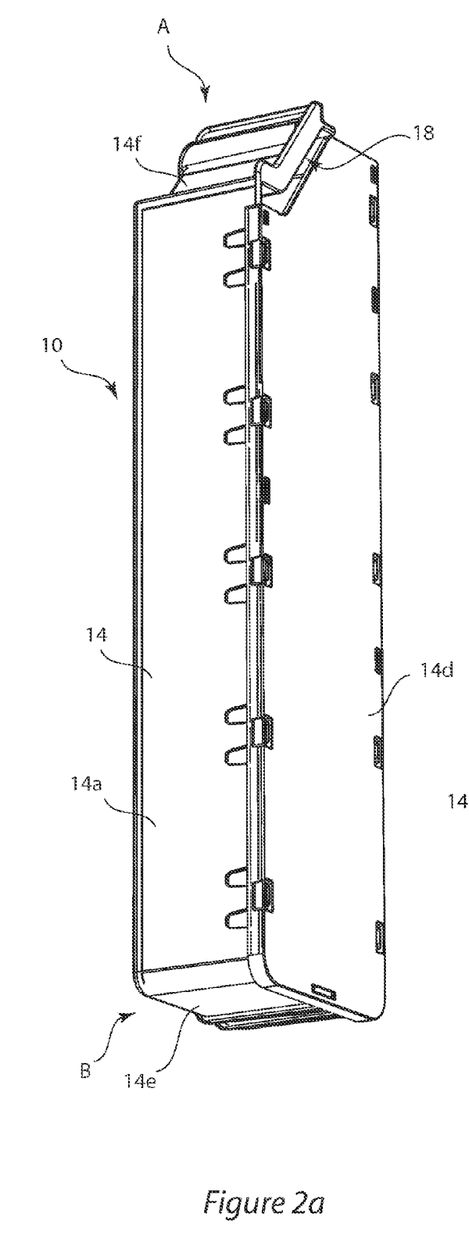
FIGS. 2a and 2b are perspective views from two other sides (and from below) of the cartridge of FIG. 1.
Figure 2B:
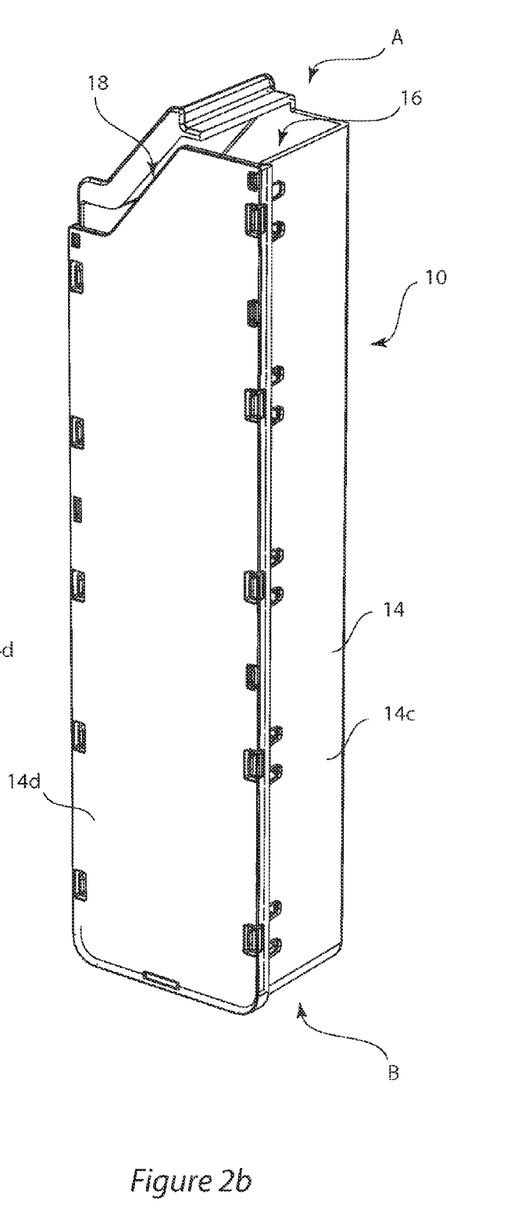
Figure 3A:
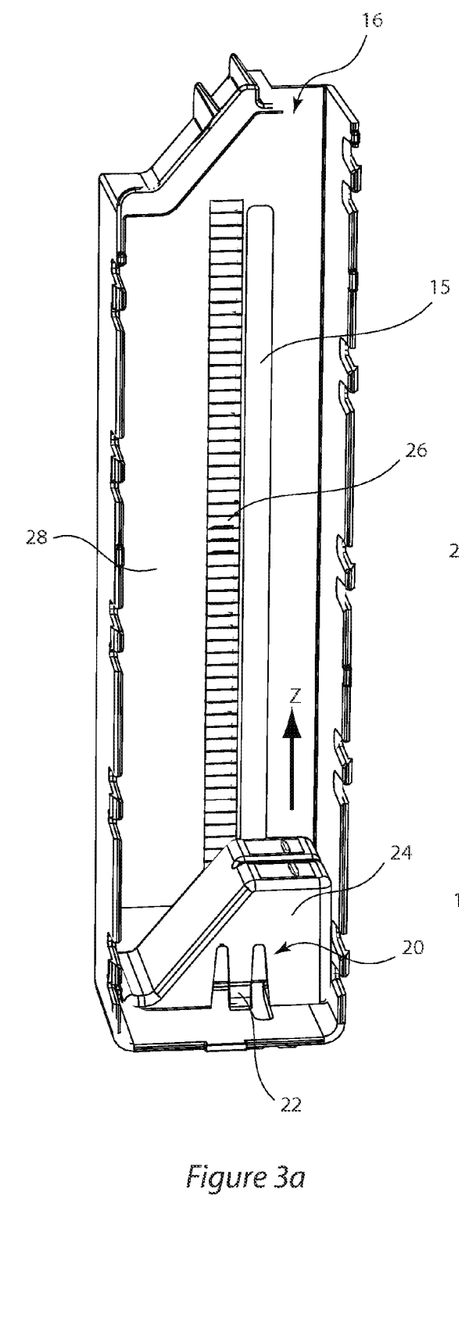
FIG. 3a is a schematic side view of the cartridge of FIG. 1, showing the interior and a streaking applicator support member.
Figure 3B:
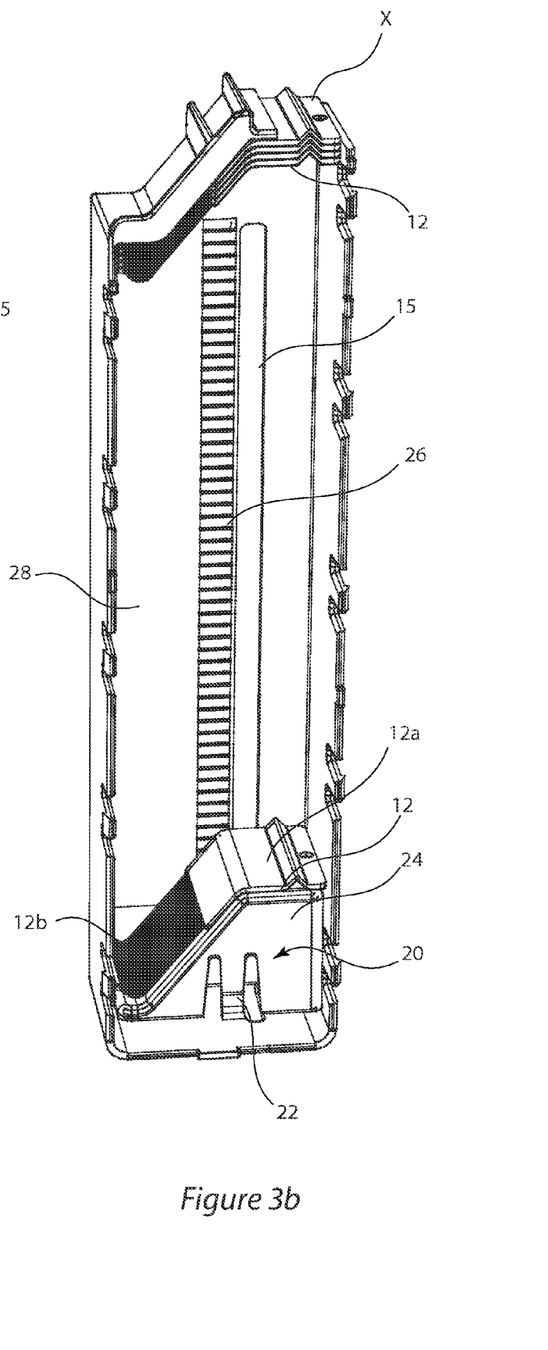
FIG. 3b is the same view together with some loaded streaking applicators.

Illustrated in FIGS. 1, 2a and 2b is a cartridge 10 for holding and dispensing streaking applicators (not shown in those figures, but identified in FIG. 3b by reference numeral 12) for an automated streaking apparatus (not shown) having a cartridge holder 28 (described later in relation to FIGS. 4a, 4b, 5 and 6). With further reference to FIG. 3b, the preferred type of streaking applicator 12 has a generally flat rectangular form, with two major inclined portions that together form a very shallow inverted v-shaped body. An upper portion of the body provides a mounting portion 12a and a lower portion 12b of the body provides the line of space apart contact surfaces towards the bottom of a resilient and flexible support member.

Returning to a description of FIGS. 1, 2a and 2b, in this embodiment the cartridge 10 includes a case 14 with a dispensing end A and a lower end B. The case 14 has a longitudinal axis Y and an elongate slot 15 therealong that is generally parallel to the longitudinal axis Y. The case 14 is generally cylindrical with a rectangular cross-section, thereby having four side walls (14a, 14b, 14c and 14d), a bottom wall 14e at the lower end B of the case 14, and a top wall 14f. This preferred orientation illustrates that the cartridge 10 is ideally elongate and is used in a generally upright orientation. In this respect, although the case 14 illustrated herein is shown as being cylindrical with a rectangular cross-section, other shapes of case are envisaged.

As shown in FIG. 1, the top wall 14f only partially covers the dispensing end A, there being one opening in the top wall 14f to provide a streaking device (identified in FIG. 5 by reference numeral 60) with gripping access to an applicator 12 in an applicator dispensing position, and at least one other opening through which the applicator 12 may pass to be removed from the cartridge 10 by the streaking device 60. The top wall 14f thus includes an upper applicator-gripping opening 16 and a side applicator-dispensing opening 18, the gripping opening 16 being sized to reveal the mounting portion 12a of an applicator 12 in the dispensing position, and the dispensing opening 18 being sized to permit that applicator 12 to be slid sideways from a stack of applicators 12 from under the top wall 14f (the position occupied by the applicator marked as X in FIG. 3b) out of the cartridge 10.

As can be seen, at least the underside of the top wall 14f is configured to conform to the shape of an applicator 12 such that the uppermost applicator X in the stack (being the applicator in the dispensing position) neatly abuts against the underside of the top wall 14f, as will be explained below, in which position the mounting portion 12a of that applicator X is accessible through the gripping opening 16 and the applicator X itself is removable via the dispensing opening 18. Thus, the uppermost applicator X in the stack of applicators is said to be operatively accessible from outside the case 14 of the cartridge 10.

The cartridge 10 also includes an applicator support member 20 that is constrained within the case 14 for longitudinal movement therein in the direction of arrow Z (shown in FIG. 3a) and is able to carry the stack of applicators. The support member 20 is also rectangular in cross-section and is sized for sliding movement within the case 14. The support member 20 is shown having ratchet-type resiliently biased engaging members 22 on two of the opposed sides 24 thereof (only one being visible in FIGS. 3a and 3b), capable of engaging with a series of corresponding abutments 26 along opposed interior surfaces 28 (only one being visible in FIGS. 3a and 3b) of two of the side walls (14b, 14d) of the case 14, in a manner that only permits one way movement of the support member 20 towards the dispensing end A of the case 14.

The elongate slot 15 is capable of operatively receiving a biasing member 30 when the cartridge 10 is in a cartridge holder 28 (shown in FIGS. 4a, 4b, 5 and 6) to urge the support member 20 towards the dispensing end A, forcing the uppermost applicator X against the underside of the top wall 14f and into the dispensing position.

Figure 4A:
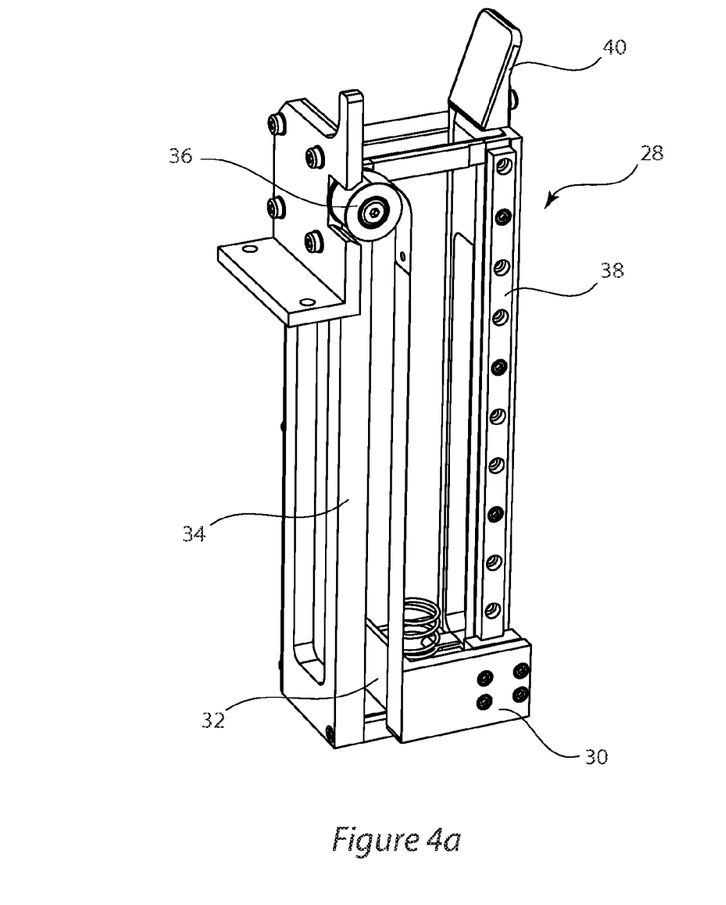
FIGS. 4a and 4b are perspective views of a cartridge holder, in different stages of operation, for use with the cartridge of FIG. 1 (but not showing the cartridge)
Figure 4B:
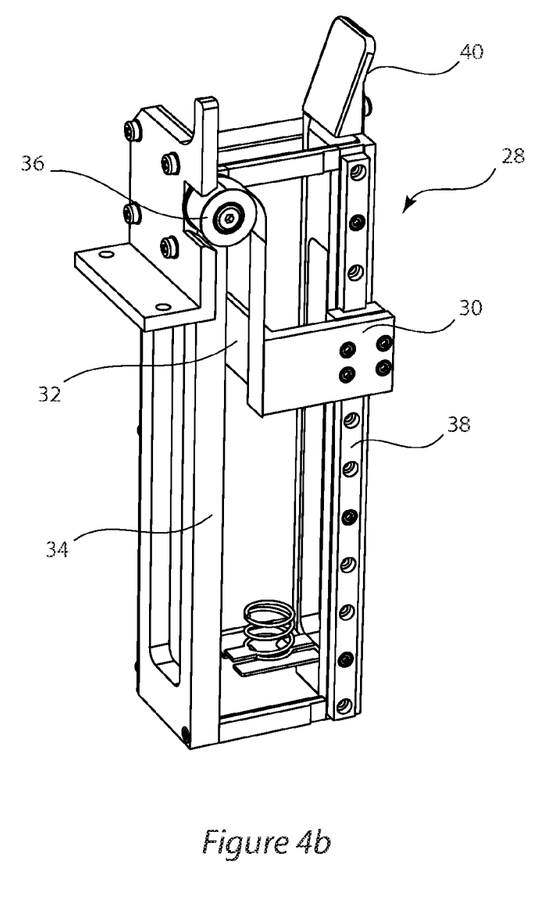
Figure 5:
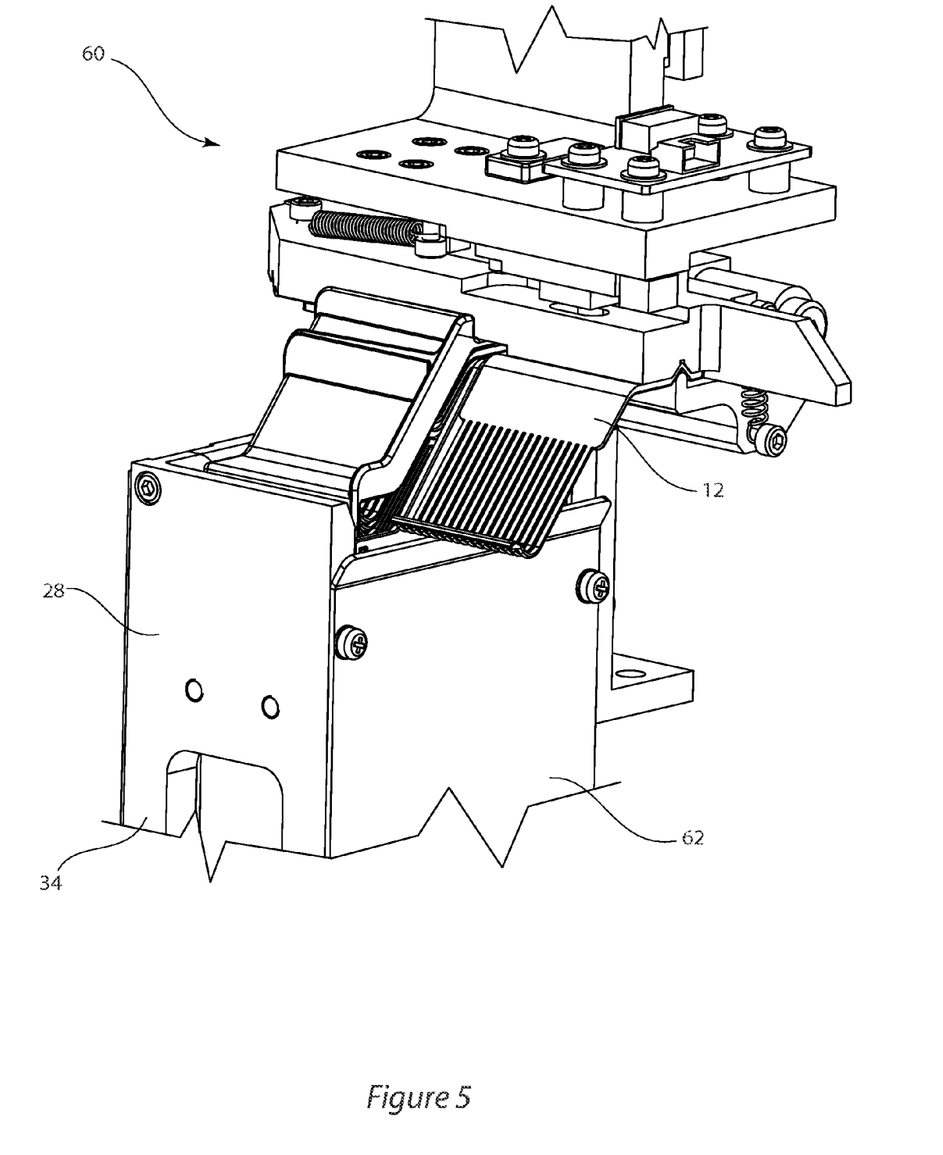
FIG. 5 is a schematic side view, in perspective, of a streaking device removing a streaking applicator from the cartridge of FIG. 1 loaded with streaking applicators and within a cartridge holder.

The biasing member 30 is a biased abutment 32 configured at least partially within the housing 34 of the cartridge holder 28, the abutment 32 being sized and located so as to fit within, and be received by, the elongate slot 15 of the cartridge 10. The biasing for the biased abutment 32 is provided by a spring, such as by a torsion spring 36 arranged to urge the biasing member 30 upwards along a guide-rail 38. FIG. 4a shows the biasing member 30 in its lowermost position (which is the position it would take if a fully loaded cartridge 10 where located within the cartridge holder 28), whereas FIG. 4b shows the biasing member 30 in a position part way towards the dispensing end A of a cartridge 10 that would be within the cartridge holder 28, when half of the applicators 12 therein had been dispensed.

The elongate slot 15 is shown arranged longitudinally along one of the side walls 14b of the case 14, extending into the bottom wall 14e of the case 14 at its lower end B to allow inserting access of the abutment 32 into the slot 15 from below when the cartridge 10 is slid into the housing 28.

Figure 6:
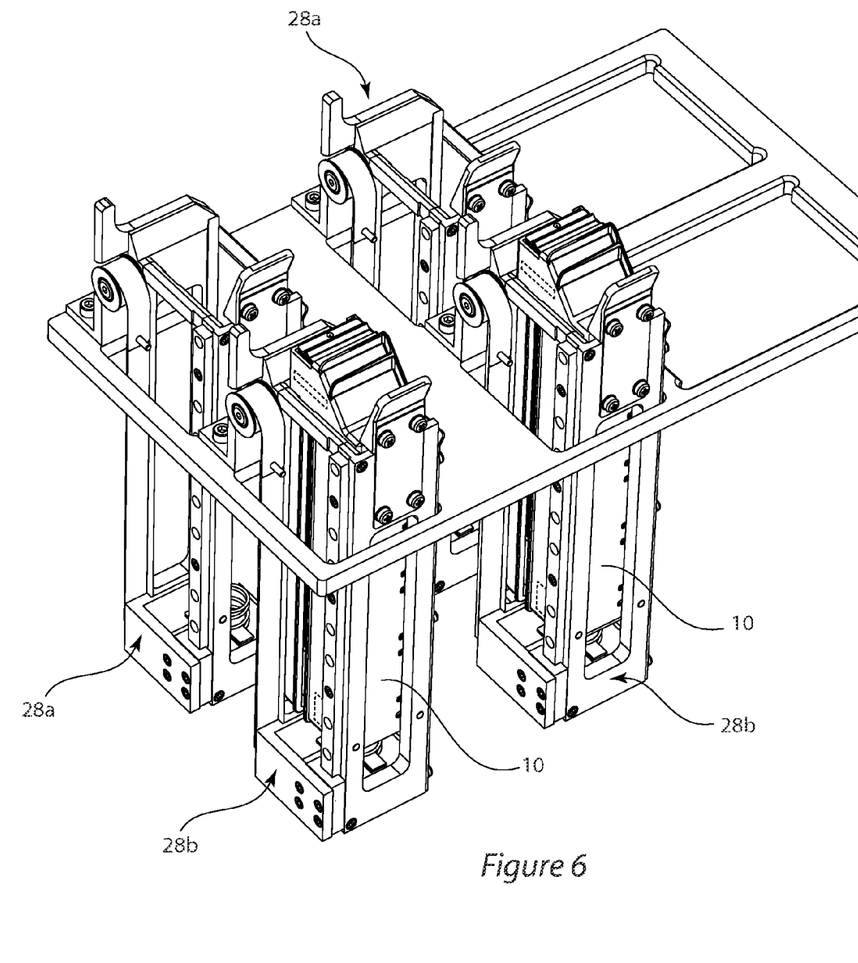
FIG. 6 is a perspective view of a series of cartridge holders in an automated streaking apparatus, two of the cartridge holders having the cartridge of FIG. 1 therein.

The cartridge holder 28 would normally form a part of the streaking apparatus generally described above, and forms a part of the overall system for the connection of a loaded cartridge 10 to a cartridge holder of an automated streaking apparatus. Indeed, FIG. 6 illustrates a part of such a streaking apparatus that includes multiple cartridge holders 28 (some of which, such as cartridge holders 28a, are shown without of a cartridge 10 therein) in order to be able to hold multiple cartridges 10 (as seen in cartridge holders 28b) and thus store, ready for dispensing, a very large number of streaking applicators 12, in a manner such that the streaking device 60 mentioned above is able to selectively access any one of the cartridges 10 to obtain a streaking applicator 12 therefrom, such as is shown in the schematic representation of FIG. 5.

Each cartridge holder 28 includes a housing 34 configured and sized so as to receive a cartridge 10 within its interior, ideally to slidably receive the cartridge 10 in a close fit therein. The housing 34 is thus shown including therewithin, the biasing member 30 mentioned above that operatively interacts with the elongate slot 15 of the casing 14 and the applicator support member 20.

The housing 34 also includes a cartridge lock 40 that releasably engages with the cartridge 10 when in the cartridge holder 28 to secure the cartridge 10 in place. Also, the biasing member 30 includes a spring 31 to assist the release of the cartridge 10 when the cartridge lock 40 is released.

Each housing 34 is shown configured and oriented such that, when a cartridge 10 is housed therein, the applicator dispensing position of the cartridge 10 (which is at the upper, dispensing end A of the cartridge 10) can be operatively accessed by the streaking device 60 of the streaking apparatus. In this respect, the housing need not be a fully enclosed housing, in that it includes complete side walls or the like, although as is evident in FIG. 5, side walls 62 can be incorporated.

Therefore, in use (and with reference to all of the figures), when a loaded cartridge 10, loaded with a stack of applicators 12 supported within the case 14 upon the support member 20, is slid into the housing 34, the abutment 32 enters the slot 15 and engages with the underside of the support member 20. The biasing of the abutment 32 is then such as to continuously urge the support member 20 towards the dispensing end A of the case 14 so that the uppermost applicator X in the stack is always urged into, and held in, the dispensing position.

The removal (or dispensing) of this uppermost applicator X (in the manner described above) by a streaking device 60 will then result in the next applicator (now becoming the uppermost applicator) in the stack again being urged by the biasing member 30 into the dispensing position. This can then continue until the last applicator 12 in the stack is dispensed and the cartridge 10 is empty.

Upon emptying of the cartridge 10, it may be removed from the automated streaking apparatus and either disposed of, or returned to a supplier for recharging. Alternatively, it may be re-filled on-site with a new stack of applicators 12. With this in mind, the case 14 of the cartridge 10 in this embodiment is formed such that one of the four walls is detachably removable to provide easy access to the interior thereof such that the cartridge 10 can be re-loaded if required. In FIGS. 3a and 3b the removable wall is the side wall 14d opposite the side wall 14b that includes the elongate slot 15.

In conclusion, it must be appreciated that there may be other variations and modifications to the configurations described herein which are also within the scope of the present invention.

We claim:

1. A cartridge for holding and dispensing streaking applicators for an automated streaking apparatus having a cartridge holder, the streaking applicators including a mounting portion and having a generally rectangular form with two major inclined portions that together form a very shallow inverted V-shaped body, the cartridge including:
   a case with a rectangular cross-section, the case having four side walls, a bottom wall and a top wall, the top wall being at a dispensing end of the case, the case also having a longitudinal axis and an elongate slot arranged longitudinally along one side wall, the dispensing end including a streaking applicator dispensing position where one streaking applicator can be at least partially accessible from outside the case;
   a streaking applicator support member constrained within the case for longitudinal movement therein and being able to carry a stack of streaking applicators;
   the dispensing end including a streaking applicator-gripping opening in the top wall and a streaking applicator-dispensing opening in a side wall, the gripping opening being sized to reveal, in use, at least a mounting portion of a streaking applicator in the dispensing position, and the dispensing opening and the gripping opening being sized to permit, in use, a streaking applicator gripped through the gripping opening to be slid sideways from the stack of streaking applicators out of the cartridge through the dispensing opening;
   the elongate slot being capable of operatively receiving a biasing member when the cartridge is in the cartridge holder to urge the support member towards the dispensing end and a streaking applicator into the dispensing position; and
   the top wall also being configured to conform to the shape of a streaking applicator such that, in use, an uppermost streaking applicator in the stack (being the streaking applicator in the dispensing position abuts against the underside of the top wall due to the urging of the biasing member, in which position the mounting portion of that streaking applicator is accessible through the gripping opening and that streaking applicator is removable via the dispensing opening.

2. A cartridge according to claim 1, wherein the applicator support member is rectangular in cross-section and is sized for sliding movement within the case.

3. A cartridge according to claim 2, wherein the support member includes resiliently biased engaging members on two opposed sides thereof, capable of engaging with a series of corresponding abutments along opposed interior surfaces of two of the side walls of the case.

4. A cartridge according to claim 3, wherein the engagement of the abutments with the engaging members only permits one way movement of the support member, in response to the urging towards the dispensing end by the biasing member of the cartridge holder, towards the dispensing end of the case.

5. A cartridge according to claim 1, wherein the biasing member is a biased abutment configured at least partially within the housing of the cartridge holder, the abutment being sized and located so as to, in use, fit within, and be received by, the elongate slot of the cartridge.

6. A cartridge according to claim 5, wherein the elongate slot extends into the bottom wall of the case to allow, in use, access therein of the biasing member from below when the cartridge is slid into the housing.

* * * * *